United States Patent
Asero et al.

(10) Patent No.: US 6,277,829 B1
(45) Date of Patent: Aug. 21, 2001

(54) PROCESS FOR PREPARING OF AQUEOUS FORMULATION FOR OPTHALMIC USE

(75) Inventors: Antonino Asero, Valverde; Maria Grazia Mazzone, Acireale; Valeria Moschetti, Gravina; Anna Rita Blanco, Acireale, all of (IT)

(73) Assignee: S.I.F.I. Societa Industria Farmaceutica Italiana S.p.A., Lavinaio (IT)

( * ) Notice: Subject to any disclaimer, the term of this patent is extended or adjusted under 35 U.S.C. 154(b) by 0 days.

(21) Appl. No.: 09/472,209

(22) Filed: Dec. 27, 1999

(30) Foreign Application Priority Data

Aug. 9, 1999 (IT) .............................................. MI99A1803

(51) Int. Cl.$^7$ ................................................. A61K 31/70
(52) U.S. Cl. ........................... 514/29; 424/114; 424/601; 424/606; 514/2; 514/8; 514/9; 514/42; 514/152; 514/153; 514/154; 514/169; 514/170; 514/171; 514/177; 514/192; 514/279; 514/299; 514/311; 514/313; 514/314; 514/568; 514/569; 514/574; 514/579; 514/601; 514/605; 514/646; 514/658; 514/716; 514/717; 514/721; 514/912; 514/914
(58) Field of Search .................................... 424/114, 601, 424/606; 514/2, 8, 9, 29, 42, 152, 153, 154, 169, 170, 171, 177, 192, 279, 299, 311, 313, 314, 568, 569, 574, 579, 601, 605, 646, 658, 716, 717, 721, 912, 914

(56) References Cited

U.S. PATENT DOCUMENTS 5,646,151 * 7/1997 Kruse et al. ........................ 514/255

FOREIGN PATENT DOCUMENTS

| 0 307 128 | 3/1989 | (EP) . |
| 0 925 789 | 6/1999 | (EP) . |
| WO 97/22335 | 6/1997 | (WO) . |

OTHER PUBLICATIONS

Remington's Pharmaceutical Sciences (17th Ed. 1985), pp. 963, 965, 972, 1119, 1553–64.*

Jiaxiang SHEN, "Azithromycin water–soluble salt, injection and their usage", *Chemical Abstracts,* vol. 130, No. 8, Feb. 22, 1999, Abstract No. 100658s, XP 002162791, XP 002162792.

* cited by examiner

*Primary Examiner*—Jose' G. Dees
*Assistant Examiner*—Frank I. Choi
(74) *Attorney, Agent, or Firm*—Oblon, Spivak, McClelland, Maier & Neustadt, P.C.

(57) ABSTRACT

The present invention describes a process for the preparation of aqueous formulations containing azithromycin for ophthalmic use, as well any formulations obtained by this process and their topical use in the ocular bacterial infections, more preferably in the treatment of conjunctivitis, keratitis and blepharitis.

14 Claims, 5 Drawing Sheets

PROCESS FOR PREPARING OF AQUEOUS FORMULATION FOR OPTHALMIC USE

BACKGROUND OF THE INVENTION

1. Field of the Invention

The present invention refers to a process for the preparation of aqueous formulations for ophthalmic use. Specifically, the present invention relates to a process for preparing ophthalmic formulations containing azithromycin, as well any formulations obtained through a such process, and their ophthalmic use against ocular bacterial infections caused by gram-positive and gram-negative pathogens (e.g. Staphylococcus spp., Streptococcus spp., *Haemophilus influenzae, Pseudomonas aeruginosa, Serratia marcescens, Klebsiella pneumoniae*, Enterobacter, Citrobacter, Chlamydia spp.) as well as from other microorganisms generally involved in the most common ocular infections (e.g. conjunctivitis, keratitis and blepharitis).

2. Description of the Background

Azithromycin (U.S. Pat. No. 4,517,359) is a well-known antibiotic belonging to the macrolide class (of which erythromycin is the precursor), antibiotics having a structural similarity, most of them isolated from fermentation of Streptomices spp., and essentially utilized in the treatment of the skin and soft tissue infections caused by gram-positive organisms, even though the spectrum of action of the newer macrolides also includes some gram-negative organisms (e.g. *Haemophilus influenzae*). Notwithstanding the structural similarity, azithromycin can be considered as unique within the macrolides class, such as to be included in a new class of antibiotics known as azalides. In particular, the specific characteristics of azithromycin make this molecule more stable, tolerated and effective than its precursor erythromycin (S. Alvarez-Elcoro, M. J. Enzler, "The macrolides: Erythromycin, clarithromycin, and azithromycin", Mayo Clinic Proceeding, 1999, 74: 613–634).

In fact, erythromycin and its salt derivatives (e.g. erythromycin lactobionate, erythromycin glucoheptonate, erythromycin estolate, erythromycin succinate etc.) have often been shown unstable in acidic medium and physiological conditions as well, by causing degradation products in microbiologically-inactive structures [P. J. Atkins et al., "Kinetic studies on the decomposition of erithromycin A in aqueous acidic and neutral buffers", Int. J. Pharmaceutics, 1986, 30: 199–207; E. Fieser, S. H. Steffen "Comparison of the acid stability of azithromycin and erithromycin A", J. Antimicrob. Chemother., 1990, (Suppl. A) 25: 39–47; M. M. Amer, K. F. Takla "Studies on the stability of some pharmaceutical formulations. V-stability of erythromycin", Bulletin of the Faculty of Pharmacy Cairo University].

In addition azithromycin, even in comparison to other recent macrolides, shows a superior antibacterial activity against some gram-negative organisms, while retaining the same efficacy against gram-positive organisms, moreover azithromycin, with respect to other macrolides, has an extensive intracellular distribution into specific tissues after oral administration (R. P. Glaude et al., Antimicrob. Agents and Chemother., 1989, 33(3): 277–82). Half-life of azithromycin is so extremely elevated such as to be considered an excellent antibiotic, after a once-daily administration, against infections of the respiratory tract, skin and soft tissues [A. P. Ball et al., J. Int. Med. Res., 1991, 19(6): 446–50; A. E. Girard et al., Antimicrob. Agents and Chemother., 1987, 31(12): 1948–1954].

Furthermore, it is also possible to administer azithromycin, by systemic route, in a variety of preparations and pharmaceutical forms. However, even though the characteristics of this molecule are such as to privilege its use as antibacterial in the topical ocular administration as well, so far it has been failed to prepare aqueous formulations for ophthalmic use, containing azithromycin, stable and compatible to the ocular structures.

Among the major difficulties to overcome, in providing an aqueous ophthalmic preparation of azithromycin, is the poor water solubility of this molecule together with safety problems resulting from the potential ophthalmic use of one of its salts, obtained by applying classical criteria of chemical synthesis, wherein the purification of the organic solvents being utilized, harmful to the ocular structures, is extremely difficult and often not completely resoluble.

As an example, EP-B-0677530 and U.S. Pat. No. 4,474,768 patents describe the preparation of different azithromycin salt derivatives, in presence of organic solvents, pharmaceutically acceptable, wherein before utilizing them in therapy, through pharmaceutical forms usually administered as oral or other incompatible forms with the topical ophthalmic use, their purification methods have to be repeated many times. It has also been described how is unlikely to overcome the difficulties of pharmaceutical type, essentially because of the poor aqueous solubility of macrolides (V. Andrews, "Antibiotic treatment of ophthalmic infection: new developments", J. Hospital Infection, 1995, 30: 268–274), and, although their acquisition in ophthalmic therapy has been wished, unless to rely on ophthalmic forms (e.g ointment) less bioavailable and which, anyway, it would make necessary their combination with eye drops of the same active principle, this in order to completely eradicate after treatment any pathogen distributed into the ocular surface.

Numerous publications describe the pharmacokinetics of azithromycin after oral administration together with its potential application to treat infections of the ocular structures [K. F. Tabbara et al., "Ocular levels of azithromycin", Arch Ophthalmol., 1998, 116(12): 1625–1628; Z. A. Karcioglu et al., "Pharmacokinetics of azithromycin in rabbit lachrymal glands and conjunctiva", Ophthalmic. Res., 1999, 31(1): 47–52; K. F. Tabbara et al., "Single-dose azithromycin in the treatment of trachoma. A randomized controlled study" Ophthalmology, 1996, 103(5): 842–846; D. M. O'Day et al., "Ocular pharmacokinetics of orally administered azithromycin in rabbits", J. Ocular Pharmacol. 1994, 10(4): 633–641; Z. A. Karcioglu et al., "Pharmacokinetics of azithromycin in trachoma patients: serum and tear levels", Ophthalmology, 1998, 105(4): 658–661]; however, under no circumstances the oral formulations utilized are able to make sure an effective tissue concentration of azithromycin into the ocular surface, what it would occur by administering topically the active principle in the elective pharmaceutical form of eye drops.

Whether from one side the synthesis of azithromycin salt derivatives has been improved or in some other instances it has been tried to increase the bioavailability as well as the activity through oral administration by adopting controlled release systems, see U.S. Pat. No. 5,705,190 referred to clarithromycin, from the other hand it has not been able to obtain similar results in preparing stable aqueous formulations, containing azithromycin, to be utilized as effective and safe products in the antimicrobial therapy of ocular infections.

SUMMARY OF THE INVENTION

It is an object of the present invention to have stable aqueous formulations for ophthalmic use containing azithromycin, providing a better corneal permeability of the active ingredient, with respect to the aqueous suspensions or lipophilic formulations, with a superior bioavailability and compatibility to the ocular structures.

It is another object of the present invention to prepare formulations whose process of preparation does not include the presence of organic solvents to be utilized either as cosolvents during the preparation of azithromycin eye drops, or as precipitating agents during the process of purification in preparing azithromycin salt derivatives by synthesis.

Moreover it is desirable to be able in realizing aqueous ophthalmic formulations containing azithromycin, which are exploitable as eye drops in the antimicrobial ophthalmic therapy.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
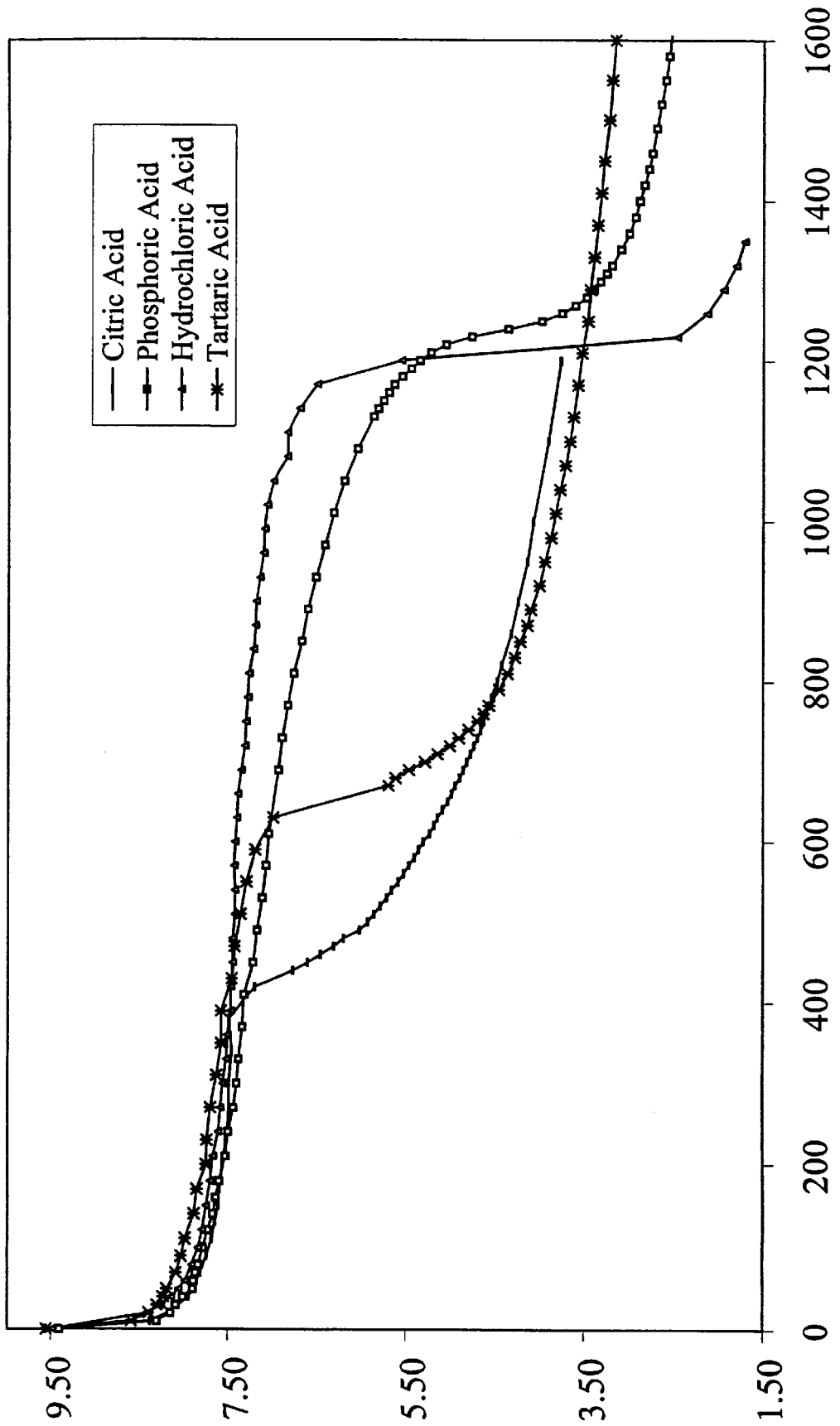
FIG. 1 shows four titration curves of azitlromycin against citric acid, phosphoric acid, hydrochloric acid and tartaric acid.

The objects described above and other of the present invention, which will become better understood from the following description, have been surprisingly achieved through a process for the preparation of an aqueous ophthalmic formulation containing azithromycin which comprises the solubilization of ophthalmically acceptable polybasic phosphate in a concentration range from 7.8 to 68.6 g/l, citric acid monohydrate in an amount ranging from 0.9 to 35.94 g/l, and the subsequent addition of azithromycin in an amount ranging from 0.1 to 100 g/l, within a temperature range from 15 to 25° C., wherein the molar ratio of azithromycin to citric acid is about 1:0.67 to 1:1.5; wherein pH is adjusted to a value of 5.5–7.6, and up to a final osmolality between about 130 to about 300 mOsm/Kg.

In one preferred embodiment of the present invention an ophthalmically acceptable polybasic phosphate is sodium phosphate, more preferably disodium phosphate dodecahydrate. The solution, under the process of the present invention, has preferably a pH ranging from about 6.4 to about 7.6, wherein the most preferred molar ratio of azithromycin to citric acid is equal to 1.5:1.

The process of the present invention allows to obtain an extremely high solubility of azithromycin in aqueous solution, also superior than 10% w/v. Formulations containing azithromycin at concentration ranging from 0.01 to 10% w/v, more particularly between 0.3 and 5% w/v, are the most preferred.

According to another preferred aspect, the process of the present invention, comprises, subsequently to the azithromycin dissolution, the addition of at least a tonicity agent and/or a viscosity-increasing agent and/or a gelling agent and/or a stabilizing agent and a preservative agent, in amounts ophthalmically acceptable.

Aqueous ophthalmic formulations obtained as defined in the process of the present invention are novel and, according to another preferred aspect, comprise, in combination with azithromycin, at least another therapeutic agent having antibacterial activity and/or a therapeutic steroidal or nonsteroidal agent having antiinflammatory activity in amounts ophthalmically acceptable to the eye.

In particular, the therapeutic agent having antibacterial activity is selected from the group consisting of aminoglycosides (e.g. netilmicin), fluoroquinolones, tetracyclines, polymyxin, glycopeptides, glycoproteins (e.g. lactoferrin), natural and/or synthetic peptides, β-lactam antibiotics, as well as other antibacterial agents, whereas the therapeutic steroidal agent having antiinflammatory activity is selected from the group made up of desonide 21-phosphate, dexamethasone, clobetasone, mometasone, betamethasone, fluticasone and other similar steroidal antiinflammatory agents. Non-steroidal agent having antiinflammatory activity is selected from the group made up of naproxen, diclofenac, nimesulide, flurbiprofen and other similar nonsteroidal antiinflammatory agents.

It is a preferred object to realize the formulations of the present invention as aqueous solutions, ointment or gel forms as well as other systems of release ophthalmically compatible to the ocular structures.

Formulations of the present invention can be advantageously utilized for the preparation of a medicine in the treatment of ocular pathologies requiring antibacterial therapy, more preferably in the treatment of conjunctivitis, keratitis and blepharitis.

FIG. 1 shows the titration curves of azithromycin, dispersed in water, with organic acids (citric acid and tartaric acid) and inorganic acids (phosphoric acid, hydrochloric acid); x-axis represents the acid concentration ($\mu$M), whereas the y-axis represents the corresponding pH. Although any addition of acid improves the solubility of the azithromycin (sigmoidal curve), citric acid allows of obtaining instantaneously an elevated concentration of azithromycin during the process for the preparation of eye drops, within a physiological range of pH.

Figure 2:
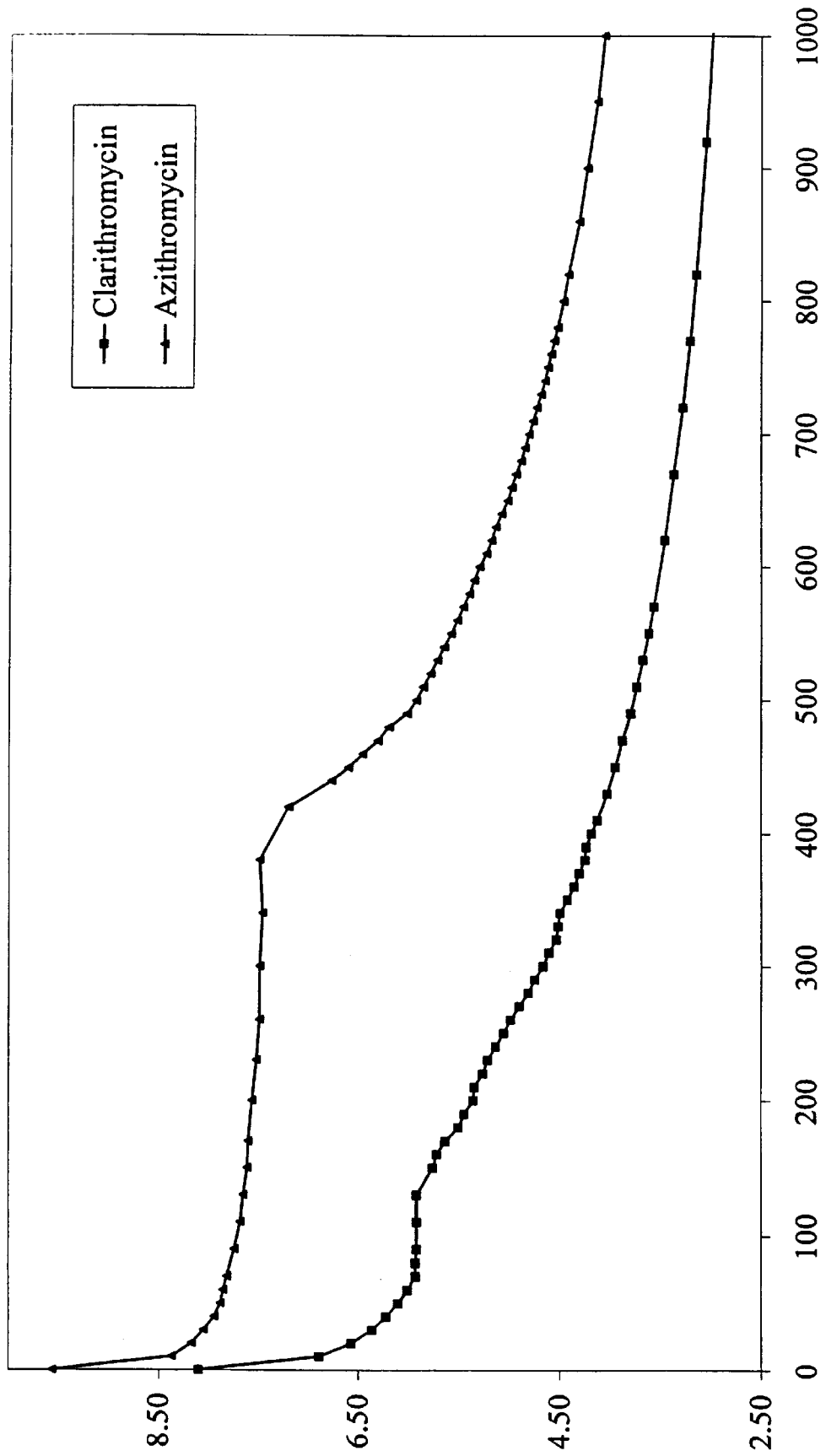
FIG. 2 shows the titration curves of azithromycin with citric acid.

FIG. 2 shows titration curves, similar to that illustrated in FIG. 1, in which azithromycin and clarithromycin are tritated with citric acid; the equivalent point for clarithromycin is about pH 4.5 instead of about pH 7.0 for azithromycin. Thus, the chemical interaction between citric acid and claritromycin does not occur at physiological pH. In addition, the maximum concentration of clarithromycin in water (<2%) is markedly lower than that achievable for azithromycin.

Figure 3:
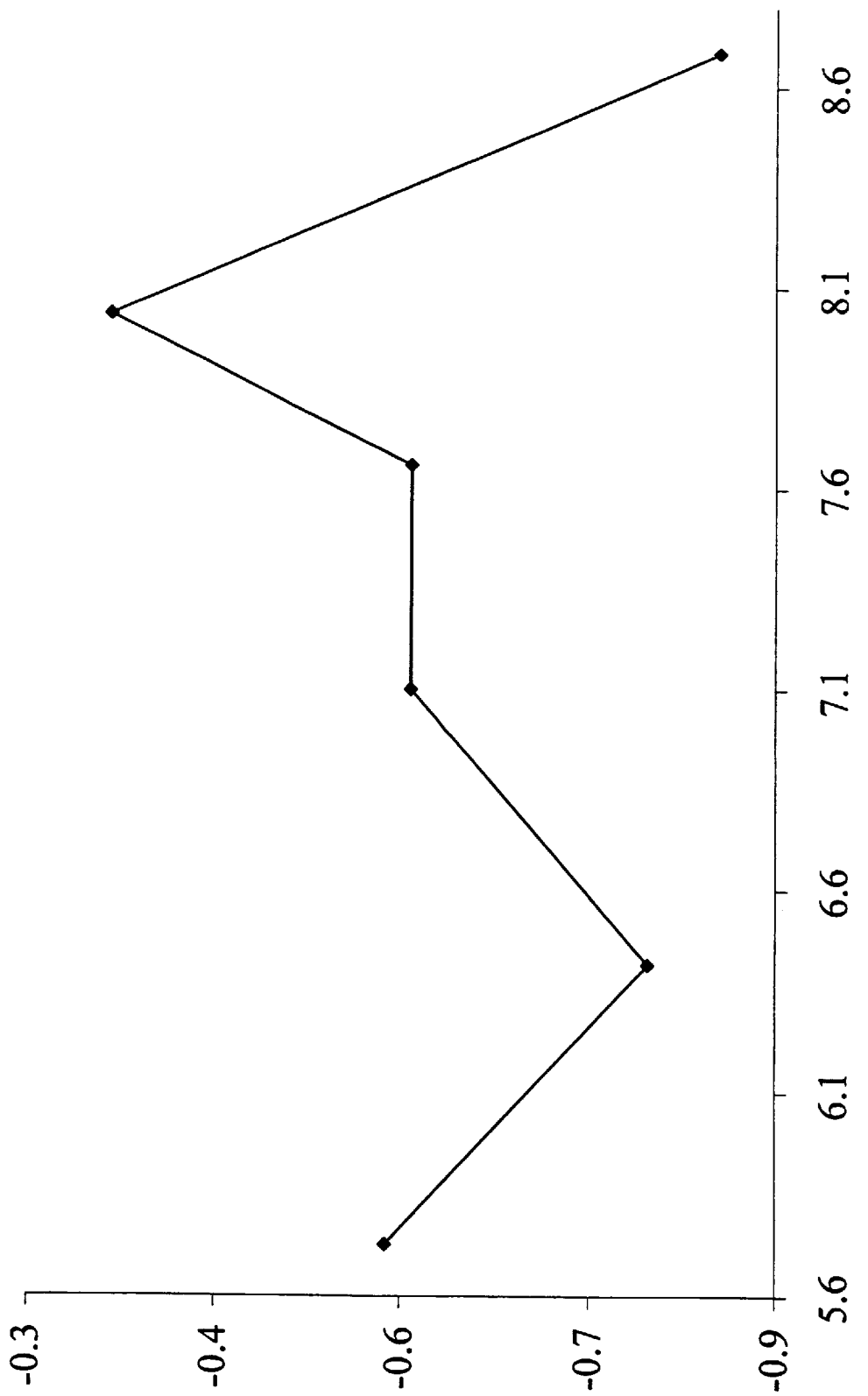
FIG. 3 shows the pH-rate stability profile of a 2% solution of azithromycin under thermal stress.

FIG. 3 shows the pH-rate stability profile of a solution containing 2% of azithromycin under thermal stress condition. Log K (week$^{-1}$) is plotted (y-axis) against pH (x-axis). Formulations of the invention are stable at pH 6.4 and pH 8.7.

Figure 4:
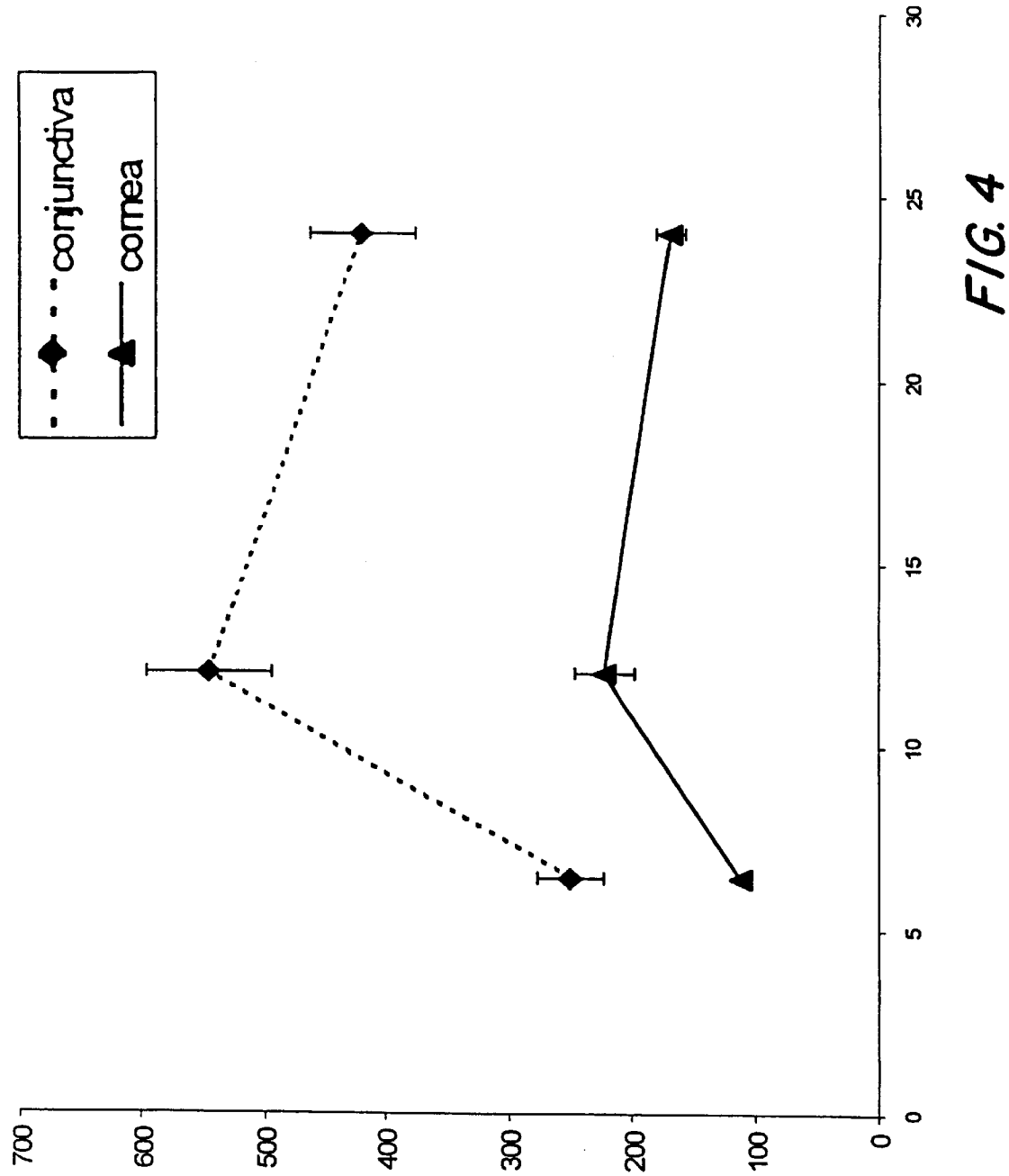
FIG. 4 shows the ocular distribution of azithromycin in cornea and conjunctiva as a function of time.

FIG. 4 shows the ocular distribution of azithromycin into the cornea and conjunctiva (T/g of tissue, y-axis) as a function of the time (hours, x-axis), after topical treatment of the animals. Tissue concentrations of azithromycin after twelve hours of treatment is approximately double with respect the initial three instillations, and these values are maintained above $MIC_{90}$ for *Staphylococcus aureus* also in the group of animals left untreated for twelve hours.

Figure 5:
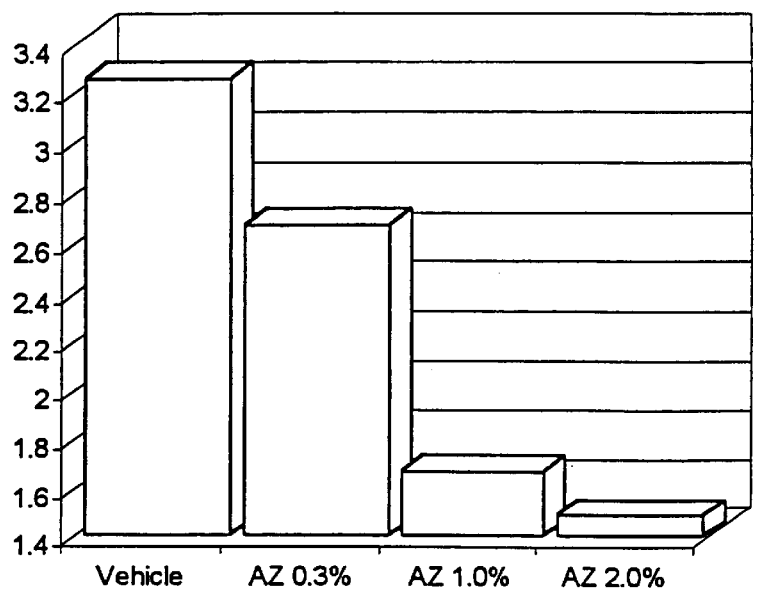
FIG. 5 shows the bacterial burden reduction in three groups of rabbits having ocular bacterial conjunctivitis treated with solutions of different concentrations as eye drops.

FIG. 5 shows the bacterial burden reduction in three groups of rabbits, having ocular bacterial conjunctivitis, treated with different solutions of azithromycin eye drops prepared under a variety of concentrations (x-axis), as defined in the process of the present invention, in which colony-forming units (cfu), expressed as log cfu/g of tissue (y-axis), are determined. In accordance with the activity profile of each tested concentration, it appears evident how the eye drops of the present invention is appropriate for the topical treatment of the ocular bacterial conjunctivitis.

Figure 6:
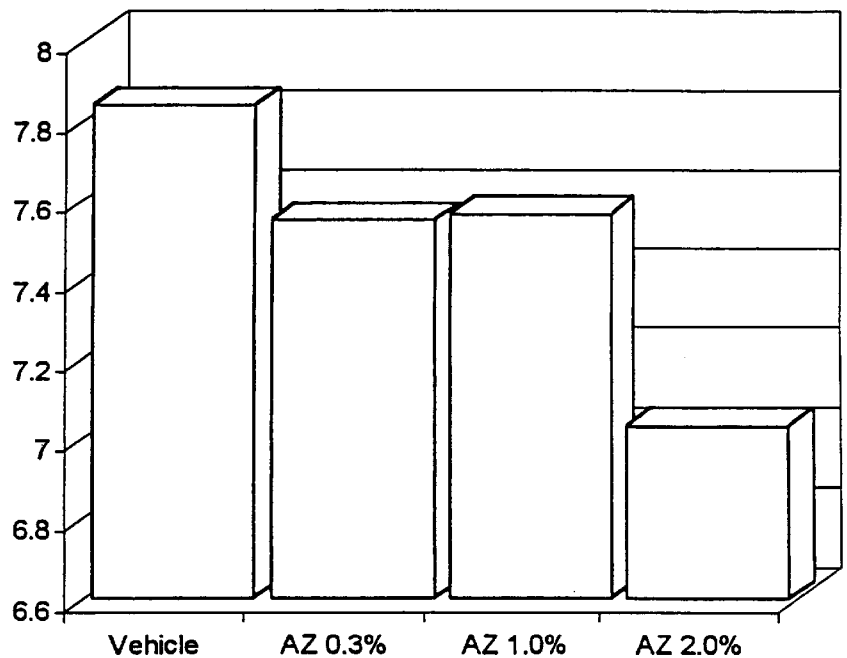
FIG. 6 shows the bacterial burden reduction in three groups of rabbits having ocular bacterial keratitis treated with solutions of azithromycin of different concentrations as eye drops.

FIG. 6 shows the bacterial burden reduction in three groups of rabbits, having ocular bacterial keratitis, treated with different solutions of azithromycin eye drops prepared under a variety of concentrations (x-axis), as defined in the present invention, in which colony-forming units (cfu), expressed as log cfu/g of tissue (y-axis), are determined.

Based on the lower mean observed for the reduction of the bacterial burden into the corneas treated with azithromycin (2%), with respect to the vehicle, it is possible to sustain that higher concentrations of azithromycin (>2%), administered as ointment or gel pharmaceutical forms and other ocular release systems as well, are effective in the ocular therapy of bacterial keratitis.

The process of the present invention is able to overcome any difficulties in preparing aqueous compositions containing azithromycin. In fact, it has been discovered a process in which, without being necessary to synthesize azithromycin salts in presence of organic solvents, it is possible, by adding appropriate amounts of citric acid/phosphate buffer ratio to the azithromycin suspension, to obtain a stable aqueous pharmaceutical form which is compatible to the ocular structures. Aqueous solutions of azithromycin prepared as defined in the process of the present patent, wherein pH ranges from 5.5 to 7.6 and osmolality ranges from 130 to 300 mOsm/Kg, are able to achieve tissue concentrations above the MIC values of the most common ocular pathogens (e.g. *Staphylococcus aureus, Staphylococcus epidermidis, Streptococcus pneumoniae Streptococcus viridans, Streptococcus pyogenes, Pseudomonas aeruginosa, Serratia marcescens, Klebsiella pneumoniae,* Enterobacter, Citrobacter, *Haemophilus influenzae,* Chlamydia spp.) making them effective in the treatment of the major ocular bacterial infections.

Ophthalmic formulations prepared as defined in the process of the present invention can comprise, in an amount ophthalmically acceptable, a polybasic phosphate buffer; viscosity-increasing agents and gelling agents (e.g. salts of hyaluronic acid, ophthalmically acceptable, with a molecular weight range of from about 200.000 to about 5.000.000 Dalton, Lutrol® F127 (BASF), Kollidon® (BASF), hydroxypropyl metilcellulose, Carbopol® (Goodrich), stabilizing agents (e.g., polyethylene glycol, propylene glycol, Cremophor® (BASF), polysorbate, ascorbate, ionic surfactants) preservatives (e.g. benzalkonium chloride, cetrimide, thimerosal, chlorobutanol, p-hydroxybenzoate, polyhexamethylen biguanide, clorexidine, sorbates), tonicity agents (sodium chloride and/or potassium chloride, glycerol, mannitol) and/or other excipients (e.g., vaseline, paraffin oil, lanolin, etc.) commonly utilized in ophthalmic formulations for human and veterinary use.

The surprising effect of the citric acid in solubilizing azithromycin, together with the unexpected opportunity to obtain elevated concentration of azalide in physiological pH range, have been exploited for preparing various azithromycin eye drops at different concentrations and pH range, in order to evaluate their stability, pharmacokinetics, safety and efficacy.

The following examples are for illustrative purposes only and are not to be interpreted as limiting the scope of the invention.

EXAMPLE 1

Preparation of Azithromycin Eye Drops

In 80 ml of water have been added, while stirring at temperature of 15–25° C., respectively as follows, disodium hydrogen phosphate dodecahydrate and citric acid monohydrate, azithromycin and benzalkonium chloride. Azithromycin has been added only when buffer agents are completely dissolved. After the complete dissolution of all the ingredients, including suitable tonicity agents, viscosity-increasing or gelling agents, stabilizing agents and additional therapeutics agents (e.g. antibiotics, nonsteroidal or steroidal antiinflammatory drugs) pH has been measured and afterward, if necessary, this value has been adjusted to pH=6.4–7.6 with 1M citric acid or 1M NaOH. The final solution (100 ml), has been sterilized and distributed in appropriate vials. Some formulations derived from this procedure are shown in the table below:

| Azithromycin (%; w:v) | $Na_2HPO_4$ $12H_2O$ (%; w:v) | Citric acid (% w:v) | |
|---|---|---|---|
| Other active(%;w:v) | | | |
| 0.3 | 3.300 | 0.223 | BK |
| 1 | 3.300 | 0.440 | BK |
| 2.0 | 3.300 | 0.536 | BK |
| 2.0 | 3.300 | 0.536 | BK, NaHA |
| 2.0 | 3.300 | 0.370 | BK, NaCl |
| 2.0 | 3.300 | 0.370 | GL, BK |
| 5.0 | 2.54 | 1.022 | BK |
| 2.0 | 3.300 | 0.440 | TH |
| Naproxen sodium salt (0.2) | | | |
| 2.0 | 3.300 | 0.440 | TH |
| Diclofenac sodium (0.1) | | | |
| 2.0 | 3.300 | 0.370 | BK, NaCl |
| Netilmicin sulfate (0.455) | | | |
| 2.0 | 3.300 | 0.440 | BK |
| Lactoferrin (2.0) | | | |
| 2.0 | 3.300 | 0.440 | BK |
| Dexamethasone sodium phosphate (0.2) | | | |
| 2.0 | 3.300 | 0.440 | BK, NaHA, PS |
| Mometasone furoate (0.2) | | | |
| 1.0 (ointment) | 0.780 | 0.229 | PO, VA, LA |
| 1.0 (ointment) | 0.780 | 0.229 | PO, VA, LA |
| Mometasone furoate (0.2) | | | |
| 2.0 | 3.300 | 0.536 | BK, LU |

GL = Glycerol: 1.5% (w:v)
BK = Benzalkonium chloride: 0.005% (w:v)
TH = Thimerosal: 0.005% (w:v)
LU = Lutrol F127: 15.5% (w:v)
NaHA = Sodium Hyaluronate: 0.15% (w:v)
PS = Polysorbate 80: 0.2% (w:v)
NaCl = Sodium Chloride: 0.800 (w:v)
PO = Paraffin oil: 20% (w:w)
VA = Vaseline: up to 100 g (w:w)
LA = Lanolin: 10 + 10% $H_2O$

EXAMPLE 2

Stability Test

Under thermal stress conditions (60° C.±2° C.) aqueous formulations show the best stability at pH=6.4 and pH=8.7

(see FIG. 3). Azithromycin formulations (EXAMPLE 1) at physiologiclal pH (6.4–7.6) and at temperature of 25° C.±2° C.; with 75%±5% of relative humidity, are still stable after 4 weeks from their initial preparation as shown in the following table.

| Formulation | Weeks | pH | Azithromycin remaining (%) |
|---|---|---|---|
| pH 5.73 | 0 | 5.73 | 100.0 |
|  | 1 | 5.60 | 98.8 |
|  | 4 | 5.64 | 96.2 |
| pH 6.42 | 0 | 6.42 | 100.0 |
|  | 1 | 6.27 | 99.6 |
|  | 4 | 6.30 | 99.8 |
| pH 7.10 | 0 | 7.10 | 100.0 |
|  | 1 | 6.97 | 100.1 |
|  | 4 | 6.96 | 100.2 |
| pH 7.66 | 0 | 7.66 | 100.0 |
|  | 1 | 7.52 | 99.5 |
|  | 4 | 7.47 | 100.2 |
| pH 8.03 | 0 | 8.03 | 100.0 |
|  | 1 | 7.41 | 96.7 |
|  | 4 | 7.38 | 89.6 |
| pH 8.68 | 0 | 8.68 | 100.0 |
|  | 1 | 8.05 | 94.1 |
|  | 4 | 8.00 | 84.0 |

Azithromicyin concentration does not affect the stability of the final product; all the solution, even after 4 weeks, are clear and colorless as well.

EXAMPLE 3

Ocular Tolerability

Twenty-four albino New Zealand rabbits (12 males and 12 females), weighing 1.9–2.0 kg, have been randomly distributed in groups (n=2) for being topically treated with azithromycin (2%) eye drops or placebo in according to the following scheme:

| Group | Treatment | | Animal number | |
|---|---|---|---|---|
|  | Right eye | Left eye | Male | Female |
| 1 | Eye drops | Untreated | 13, 14, 15, 16, 17, 18 | 1, 2, 3, 4, 5, 6 |
| 2 | Placebo | Untreated | 19, 20, 21, 22, 23, 24 | 7, 8, 9, 10, 11, 12 |

Eight treatments the first day and four the following days have been performed. A drop (50 µl) of azithromycin (2%) eye drops or placebo has been administered into the conjunctival cul-de-sac of the animal. After the administration the lid has been maintained close for a couple of seconds in order to reduce loss of solution and to permit its distribution into the eye. Differences between each treated group and their corresponding control have been assessed by Mann-Whitney test.

By using a slit-lamp, clinical examination of the eyes has been performed at 0, ¼, ½, 1, 2, 3, 4, 5, 6, 7, 8, 24, 48, 72, 96, 168, 240, 360, 480 and 672 hours after the beginning of the study. Ocular tolerability/toxicity has been established by recording the clinical signs in the conjunctiva (congestion, edema, exudate), cornea (opacity) and iris (dilation) according to the scoring system developed by Draize. The degree of severity of each sign has been graded from 0–3 (0∀normal, 1∀mild, 2∀moderate, 3∀severe). After clinical observation, four corneas for each group of rabbits have been processed for scanning electron microscopy (SEM). In addition, after treatment various organs and tissues have been stored away for the histopathologic examination.

No clinical signs indicating any effect related to the azithromycin (2%) eye drops has been observed during the 28-days treatment. The Draize test has not shown significant difference between azithromycin (2%) eye drops and placebo. Analysis by SEM and histopathologic examination as well shown no treatment-related change in the tissues and organs examined (eye, heart, brain, liver, kidney, lung, colon and stomach). As a result azithromycin (2%) eye drops appears to be well tolerated following topical instillation into the eye of albino rabbits during a 28-days period.

EXAMPLE 4

Azithromycin Distribution in Conjunctiva, Cornea, and Aqueous Humor after Topical Application in the Eye of Albino Rabbits A pharmacokinetic study it has been carried out in order to estimate the concentration of azithromycin in the cornea, conjunctiva and aqueous humor. Twelve male white New Zealand rabbits (weighing 1.8–2.3 kg) have been randomly divided in three groups (consisting of four animals each). Subsequently, all rabbits have been instilled in the lower conjunctival cul-de-sac of both eyes, every two hours, with 50 Tl of azithromycin (2%) according to the following dosing scheme:

I Group: three instillations (animals have been sacrificed 6 hours after the first dosing)

II Group: six instillations (animals have been sacrificed 12 hours after the first dosing)

III Group: six instillations (animals have been sacrificed 24 hours after the first dosing)

Rabbits have been sacrificed by an overdose of Tanax$^R$ injected into the marginal ear vein, the eyes treated with azithromycin have been washed with phosphate-buffered saline (PBS 0.1M; pH 7) and each conjunctiva has been surgically removed just before enucleation. Aqueous humor has been drawn away with a 23-gauge needle attached to an insulin syringe of 1 ml. After enucleation the cornea has been excised at the limbus and removed from the eyeball. All specimens have been carefully weighed, then immediately frozen at −20° C. Tissue or aqueous humor concentrations of azithromycin have been determined by the following microbiologic method. Each specimen has been ground and homogenized with 1 ml of PBS (2 min., 24,000 rpm). The suspension has been mixed with an equal volume of acetonitrile and stored at 0° C. After 1 hour, the samples have been centrifuged at 0° C. (12,000 rpm; 10 min) and the aqueous supernatant layer has been evaluated for the azithromycin measurement in each specimen. Aqueous humor has been directly mixed with acetonitrile before being centrifuged. Azithromycin concentrations for each cornea, conjunctive and aqueous humor have been determined in triplicate, averaged for each tissue sample, and compared to a standard curve. It has been confirmed a linear relationship between azithromycin concentration (log) and its related inhibition zone against *Staphylococcus aureus* ATCC 29213 as shown from the following regression lines determined for each sample:

| Sample | Regression line |
|---|---|
| Cornea | Y = 6.3312 x + 7.5975; r = 0.9980 |
| Conjunctiva | Y = 6.2464 x + 7.3909; r = 0.9999 |
| Aqueous humor | Y = 9.2474 x + 4.6451; r = 0.9864 |

The bioassay method has a detection limit of 3.8 Tg/ml in the aqueous humor.

Azithromycin concentration increased in both cornea and conjunctive during the first twelve hours (see tables below and FIG. 4). In particular, tissue concentration of azithromycin after 12 hours (six instillations) is about twice as much that evaluated after six hours of treatment. Finally, even after 24 hours and 6 instillations the concentration of azithromycin in both cornea and conjunctive is still maintained above $MIC_{90}$ for Staphylococcus aureus (2.25 Tg/ml). These data confirm that formulations, containing azithromycin, can be effectively utilized for the treatment of ocular bacterial infections such as conjunctivitis, blepharitis, and keratitis. No azithromycin concentration has been detected in aqueous humor (<3.8 Tg/ml).

CORNEA

| Group | Eye N. | Zone (mm) | Cs (µg/ml) | Tissue weight (g) | Ct (µg/g) |
|---|---|---|---|---|---|
| 3 instillations animals sacrificed after 6 hours | 1 | ND | | 0.0421 | <100 |
| | 2 | ND | | 0.0415 | <100 |
| | 3 | ND | | 0.0433 | <100 |
| | 4 | ND | | 0.0436 | <100 |
| | 5 | 10.00 | 2.62 | 0.0465 | 113 |
| | 6 | ND | | 0.0417 | <100 |
| | 7 | ND | | 0.0431 | <100 |
| | 8 | 10.00 | 2.62 | 0.0482 | 109 |
| 6 instillations animals sacrificed after 12 hours | 9 | 12.00 | 5.47 | 0.0406 | 269 |
| | 10 | 12.75 | 7.21 | 0.0494 | 292 |
| | 11 | 11.25 | 4.15 | 0.0520 | 159 |
| | 12 | 10.25 | 2.87 | 0.0512 | 113 |
| | 13 | 12.00 | 5.47 | 0.0483 | 226 |
| | 14 | 12.75 | 7.21 | 0.0460 | 313 |
| | 15 | 12.25 | 6.00 | 0.0530 | 226 |
| | 16 | 11.00 | 3.78 | 0.0414 | 183 |
| Average 222.5; Sd 68.7; s.e.m 24.2 | | | | | |
| 6 instillations animals sacrificed after 24 hours | 17 | 11.75 | 4.99 | 0.0462 | 216 |
| | 18 | 11.75 | 4.99 | 0.0586 | 170 |
| | 19 | 11.00 | 3.78 | 0.0482 | 157 |
| | 20 | 11.00 | 3.78 | 0.0522 | 145 |
| | 21 | 10.50 | 3.14 | 0.0480 | 131 |
| | 22 | 11, 00 | 3.78 | 0.0550 | 137 |
| | 23 | 11, 25 | 4.15 | 0.0468 | 177 |
| | 24 | 12, 00 | 5.47 | 0.0495 | 221 |
| Average 169.3; Sd 34.2; s.e.m. 12.1 | | | | | |

Cs: Suspension concentration of azithromycin (µg/ml)
Ct: Tissue concentration of azithromycin (µg/g)
ND: Not Detected
Sd: Standard deviation
s.e.m: standard error of the mean

CONJUNCTIVA

| Group | Eye N. | Zone (mm) | Cs (µg/ml) | Tissue weight (g) | Ct (µg/g) |
|---|---|---|---|---|---|
| 3 instillations animals sacrificed after 6 hours | 1 | ND | | 0.0148 | <200 |
| | 2 | ND | | 0.0328 | <200 |
| | 3 | ND | | 0.0342 | <200 |
| | 4 | 11.00 | 4.24 | 0.0294 | 288 |
| | 5 | 11.00 | 4.24 | 0.0393 | 216 |
| | 6 | 10.00 | 3.01 | 0.0284 | 212 |
| | 7 | 10.00 | 3.01 | 0.0307 | 196 |
| | 8 | 10.50 | 3.57 | 0.0212 | 337 |
| Average 249.8; Sd 60.3; s.e.m 26.9 | | | | | |
| 6 instillations animals sacrificed after 6 hours | 9 | 11.75 | 5.48 | 0.0084 | 1305 |
| | 10 | 13.00 | 8.39 | 0.0281 | 597 |
| | 11 | 12, 25 | 6.50 | 0.0203 | 640 |
| | 12 | 12.00 | 5.96 | 0.0258 | 462 |
| | 13 | 11.75 | 5.48 | 0.0136 | 806 |
| | 14 | 11.00 | 4.24 | 0.0191 | 444 |
| | 15 | 12.00 | 5.96 | 0.0268 | 445 |
| | 16 | 11.75 | 5.48 | 0.0262 | 418 |
| Average 544.5; Sd 143.2; s.e.m 54.1 | | | | | |
| 6 instillations animals sacrificed after 24 hours | 17 | 11.25 | 4.62 | 0.0188 | 491 |
| | 18 | 11.25 | 4.62 | 0.0175 | 528 |
| | 19 | 10.75 | 3.89 | 0.0248 | 314 |
| | 20 | 11.00 | 4.24 | 0.0228 | 372 |
| | 21 | 10.00 | 3.01 | 0.0260 | 232 |
| | 22 | 10.00 | 3.01 | 0.0115 | 523 |
| | 23 | ND | | 0.0131 | |
| | 24 | 11.00 | 4.24 | 0.0176 | 482 |
| Average 420.3; Sd 115.5; s.e.m 43.7 | | | | | |

Cs: Suspension concentration of azithromycin (µg/ml)
Ct: Tissue concentration of azithromycin (µg/g)
ND: Not Detected
Sd: Standard deviation
s.e.m: standard error of the mean

EXAMPLE 5

In Vitro Antibacterial Activity

In vitro bacteriostatic/bactericidal activity of azithromycin in different ophthalmic solutions has been evaluated as a function of ([H+]). Assessment of the activity it has been carried out by standardized method recommended by the National Committee for Clinical Laboratory Standards (NCCLS). In particular, three azithromycin solutions at different pH (6.5, 7.2, 7.8) in citrate-phosphate have been examined. Accordingly, three aliquots of Mueller-Hinton broth have been adjusted to the same pH of the azithromycin solutions (three) to be tested.

MIC values (µg/ml) have been measured by turbidity standard method after incubation of azithromycin aliquots, at the different pH, ranging from 18 to 24 h. Incubation for Staphylococcus spp. and Pseudomonas spp. needs aerobic conditions whereas Streptococcus spp. and Haernophilus spp. require partial anaerobic conditions during the period of incubation (5%, $CO_2$).

Concentration of azithromycin able to inhibit the growth of the bacteria, after the period of incubation, is defined as the minimum inhibitory concentration (MIC).

Minimum bactericidal concentration (MBC) has been evaluated, by plating into appropriate culture medium, 0.1 ml of each azithromycin concentration above MIC. MBC of azithromycin is defined as the lowest concentration able to determine a bacterial growth less than 10 colony forming units (cfu).

As shown in the following table, antimicrobial activity (MBC and MIC) of the three tested ophthalmic solutions are affected from pH. In particular, it has been established that is possible to select an appropriate pH range wherein the ophthalmic solutions are shown still effective to inhibit the activity of azithromycin against the most important pathogens causing ocular infections.

| MIC (µg/ml) | pH 6.5 | 7.2 | 7.8 | MBC (µg/ml) | pH 6.5 | 7.2 | 7.5 |
|---|---|---|---|---|---|---|---|
| S. aureus ATCC 6538P | 2.25 | 1 | 0.75 | S. aureus ATCC 6538P | >4 | 2.5 | 1.75 |
| S. aureus ATCC 29213 | 3.25 | 2.25 | 1 | S. aureus ATCC 29213 | >4 | >4 | 2.25 |
| S. aureus ATCC 25923 | 3 | 1.5 | 0.75 | S. aureus ATCC 25923 | >4 | 3.25 | 2 |
| S. epidermidis ATCC 12228 | 2.5 | 1.5 | 0.75 | S. epidermidis ATCC 12228 | >4 | 3 | 2 |
| St. Pneumoniae ATCC 49619 | 1.25 | 0.25 | 0.15 | St. Pneumoniae ATCC 49619 | 3 | 0.45 | 0.3 |
| St. Pryogenes ATCC 21547 | 1.5 | 0.37 | 0.20 | St. Pyogenes ATCC 21547 | 3 | 0.6 | 0.35 |
| H. influenzae ATCC 9006 | 3 | 2 | 0.5 | H. influenzae ATCC 9006 | 6 | 3.5 | 3.5 |
| H. influenzae ATCC 49247 | 3 | 2 | 1 | H. influenzae ATCC 49247 | 7 | 3.5 | 3 |
| Ps. aeruginosa ATCC 9027 | 200 | 25 | 6.25 | Ps. aeruginosa ATCC 9027 | — | >200 | 200 |
| Ps. aeruginosa ATCC 27853 | >200 | 50 | 12.5 | Ps. aeruginosa ATCC 27853 | — | 100 | 50 |

EXAMPLE 6

Antimicrobial Activity of Azithromycin Eye Drops

To test, reproducibly, the antimicrobial activity of azithromycin eye drops, a rabbit model of conjunctivitis has been designed. An abrasion along the inner surface of the lower lid together with a radial 4-mm incision near the medial canthus has been caused on both eyes of fifteen white New Zealand rabbits (1.8–2.0 kg). Soon after 100 Tl of suspension containing 1×10$^8$//ml S. aureus of a clinical ocular isolate have been administered in the conjunctival cul-de-sac of both eyes every two hours for three times. Slit lamp examination has been performed and the signs of ocular infection monitored up to 5 day, at 24-h intervals, according to the modified McDonald-Shadduck scale. Immediately after the examination for clinical scoring, groups of two or three rabbits have been sacrificed by intravenous injection of Tanax$^R$. At 24 h from the injury S. aureus produces conjunctivitis in the rabbits that remains throughout the 5-days period of ocular observation. Hyperemia and purulent discharge have been the most pronounced and persistent signs scored. This experimental model of conjunctivitis then has been applied for testing the antimicrobial activity of azithromycin eye drops (0.3%, 1%, 2%).

Fifteen male albino New Zealand rabbits, weighing 1.8–2 Kg, have been randomly distributed in groups (n=3) for being topically treated with test samples or placebo eye drops 24 h after the bacterial inoculation of *staphylococcus aureus*. The experimental design is summarized as follows:

| Group | Eye | N. of eyes | Infection present | Treatment | Test substance |
|---|---|---|---|---|---|
| I | R | 5 | Yes | 50 µl every 2h for 12h | 2% eye drops |
|   | L | 5 | Yes | 50 µl ever 2h for 12h | Vehicle only |
| II | R | 5 | Yes | 50 µl every 2h for 12h | 1% eye drops |
|   | L | 5 | Yes | 50 µl every 2h for 12h | Vehicle only |
| III | R | 5 | Yes | 50 µl every 2h for 12h | 0.3% eye drops |
|   | L | 5 | Yes | 50 µl every 2h for 12h | Vehicle only |

R = Right
L = Left

One hour after the last administration, animals have been sacrificed by intravenous injection of Tanax$^R$. Conjunctivae, surgically removed, have been ground in an appropriate volume of H$_2$O 0.1% peptone with Stomacher® 80 Lab System (pbi international). Aliquots of the supernatant have been filtered and the residue samples have been placed on blood agar plates (Columbia CNA agar). The plates have been incubated at 37° C. for 24 h, after which colony-forming units (cfu), expressed as log cfu/g of tissue have been determined for each conjunctiva.

The bacterial burden reduction in the three groups of rabbits treated with different eye drops solution of azithromycin is shown in FIG. 5. Based on this activity profile, azithromycin eye drops is considered a promising candidate for the treatment of ocular bacterial conjunctivitis.

EXAMPLE 7

Antimicrobial Activity of Azithromycin Eye Drops

A rabbit model of keratitis has been realized by application of S. aureus into the central corneal stroma. Both eyes of eight white New Zealand rabbits (1.8–2.0 kg) have been intrastromally injected with 10 Tl of suspension containing ~1×10$^3$ ufc/ml of *Staphylococcus aureus* ocular isolate. Clinical examination by slit lamp has been performed and the correspondent signs of ocular infection monitored up to 3 day, at 24-h intervals, according to the modified McDonald-Shadduck scale. After each observation, groups of two rabbits have been sacrificed by intravenous injection of Tanax$^R$ in the marginal vein of the ear. Corneas, immediately removed after sacrifice, have been analyzed for the determination of bacterial burden. Twenty-four hours from S. aureus infection the lost of corneal transparency is particularly evident in the region of the inoculation. It has also been observed a conjunctival involvement with diffuse redness, and an elevated mucupurulent secretion. The clinical representation of the subsequent observations at 48–72 h makes worse with a complete lost of corneal transparency and purulent discharge. This experimental model of keratitis has been hereafter applied for testing the antimicrobial activity of azithromycin eye drops (0.3%, 1%, 2%).

Sixteen male albino New Zealand rabbits, weighing 1.8–2.0 Kg, have been randomly distributed in groups (n=3) for being topically treated with test substance or placebo eye drops 24 h after the bacterial inoculation. The experimental design is summarized as follows:

| Group | Eye | N. of eyes | Infection present | Treatment | Test substance |
| --- | --- | --- | --- | --- | --- |
| I | R | 4 | Yes | 50 µl every 2h for 12h | 2% eye drops |
|  | L | 4 | Yes | 50 µl ever 2h for 12h | Vehicle only |
| II | R | 6 | Yes | 50 µl every 2h for 12h | 1% eye drops |
|  | L | 6 | Yes | 50 µl every 2h for 12h | Vehicle only |
| III | R | 6 | Yes | 50 µl every 2h for 12h | 0.3% eye drops |
|  | L | 6 | Yes | 50 µl every 2h for 12h | Vehicle only |

R = Right
L = Left

One hour after the last instillation, animals have been sacrificed by intravenous injection of Tanax$^R$. Corneas, surgically removed, have been ground in 3 ml of $H_2O$ 0.1% peptone and homogenized. Aliquots of supernatant have been serially diluted (1:10) and 0.1 ml of each final suspension, including the undiluted sample, have been spread on blood agar plates (Columbia CNA agar). The plates have been incubated at 37° C. for 24 h, after which colony-forming units (cfu), expressed as log cfu/g of tissue, have been determined for each cornea.

The bacterial burden reduction in the three groups of rabbits treated with different eye drops concentrations of azithromycin is shown in FIG. 6. Mean values of the bacterial burden reduction into the corneas treated with azithromycin (2%) are slightly lower than those treated with vehicle. However, in view of the fact that a favorable pharmacokinetic profile into the cornea has been determined (see EXAMPLE 4) then it is possible to believe that more elevated concentration of azithromycin (>2%), to be administered also as ointment or gel or other release systems forms, may result sufficiently effective in the ocular therapy of bacterial keratitis.

What is claimed is:

1. A process for the preparation of an aqueous azithromycin containing ophthalmic formulation, comprising:

dissolving, in an aqueous medium, ophthalmically acceptable polybasic phosphate in an amount ranging from 7.8 to 68.6 g/l and citric acid monohydrate in an amount ranging from 0.9 to 35.94 g/l; and solubilizing azithromycin in the aqueous medium in an amount ranging from 0.1 to 100 g/l at a temperature of 15 to 25° C. wherein the molar ratio of azithromycin to citric acid ranges from 1:0.67 to 1:1.5, the pH is adjusted to range from 5.5 to 7.6 and the final osmolality ranges from 130 to 300 mOsm/kg.

2. The process as defined in claim 1, wherein the molar ratio of azithromycin to citric acid is 1.5:1.

3. The process as defined in claim 1, wherein the ophthalmically acceptable polybasic phosphate is disodium hydrogen phosphate dodecahydrate.

4. The process as defined in claim 1, wherein pH ranges from 6.4 to 7.6.

5. The process as defined in claim 1, which further comprises, after the solubilization of azithromycin, adding at least a tonicity agent and/or a viscosity-increasing agent and/or a gelling agent and/or a stabilizing agent and a preserving agent in the aqueous medium, in ophthalmically acceptable amounts.

6. An aqueous ophthalmic formulation prepared by the process as defined in claim 1.

7. The formulation as defined in claim 6, wherein the concentration of azithromycin is equal to 0.01–10% w/v.

8. The formulation as defined in claim 6, which comprises, in combination with azithromycin, at least another, ophthalmically acceptable, therapeutic agent having antibacterial activity and/or a therapeutic steroidal or nonsteroidal agent having antiinflammatory activity.

9. The formulation as defined in claim 8, wherein the therapeutic agent having antibacterial activity is selected from the group consisting of aminoglycosides, fluoroquinolones, tetracyclines, polymyxin, glycopeptides, glycoproteins, natural and/or synthetic peptides, and β-lactam derivatives.

10. The formulation as defined in claim 8, wherein the steroidal antiinflammatory agent is selected from the group consisting of desonide 21-phosphate, dexamethasone, clobetasone, mometasone, betametasone and fluticasone.

11. The formulation as defined in claim 8, wherein the nonsteroidal antiinflammatory agent is selected from the group consisting of naproxen, diclofenac, nimesulide and flurbiprofen.

12. The formulation as defined in, claim 6, in the form of an aqueous solution, ointment or gel.

13. A method of treating ocular pathologies, comprising:

applying an effective amount of the aqueous ophthalmic formulation of claim 6 to ocular surfaces requiring antibacterial therapy.

14. The method according to claim 13, wherein the ocular pathology is conjunctivitis, keratitis or blepharitis.

* * * * *

UNITED STATES PATENT AND TRADEMARK OFFICE
CERTIFICATE OF CORRECTION

PATENT NO. : 6,277,829 B1
DATED : August 21, 2001
INVENTOR(S) : Asero et al.

It is certified that error appears in the above-identified patent and that said Letters Patent is hereby corrected as shown below:

<u>Title page, Item [54], and Column 1, Line 1,</u>
The title should be:

-- [54] PROCESS FOR THE PREPARATION OF AQUEOUS FORMULATIONS FOR OPHTHALMIC USE --

Signed and Sealed this

Twenty-sixth Day of February, 2002

Attest:

JAMES E. ROGAN
Attesting Officer
Director of the United States Patent and Trademark Office